US010060916B2

(12) United States Patent
Knopfmacher

(10) Patent No.: US 10,060,916 B2
(45) Date of Patent: Aug. 28, 2018

(54) ELECTRICAL BIOSENSOR FOR DETECTING A SUBSTANCE IN A BODILY FLUID, AND METHOD AND SYSTEM FOR SAME

(71) Applicant: Avails Medical, Inc., Palo Alto, CA (US)

(72) Inventor: Oren S. Knopfmacher, Palo Alto, CA (US)

(73) Assignee: Avails Medical, Inc., Menlo Park, CA (US)

( * ) Notice: Subject to any disclaimer, the term of this patent is extended or adjusted under 35 U.S.C. 154(b) by 70 days.

(21) Appl. No.: 15/159,625

(22) Filed: May 19, 2016

(65) Prior Publication Data

US 2016/0266102 A1    Sep. 15, 2016

Related U.S. Application Data

(63) Continuation of application No. PCT/US2014/066931, filed on Nov. 21, 2014.
(Continued)

(51) Int. Cl.
*G01N 33/543* (2006.01)
*G01N 27/414* (2006.01)
(Continued)

(52) U.S. Cl.
CPC ..... *G01N 33/5438* (2013.01); *G01N 27/4145* (2013.01); *G01N 33/48792* (2013.01); *G01N 33/53* (2013.01)

(58) Field of Classification Search
CPC ............... G01N 33/5438; G01N 33/53; G01N 33/48792; G01N 27/4145
See application file for complete search history.

(56) References Cited

U.S. PATENT DOCUMENTS 4,236,893 A    12/1980  Rice
4,314,821 A     2/1982  Rice
(Continued)

FOREIGN PATENT DOCUMENTS

WO    WO 2003/044530    5/2003
WO    WO 2007/035814    3/2007
(Continued)

OTHER PUBLICATIONS

Dortet, Laurent et al., "CarbAcineto NP Test for Rapid Detection of Carbapenemase-Producing *Acinetobacter* spp.", Journal of Clinical Microbiology, 52(7):2359-2364, Jul. 2014.
(Continued)

*Primary Examiner* — Melanie Yu Brown
(74) *Attorney, Agent, or Firm* — Levine Bagade Han LLP

(57) ABSTRACT

An electrical biosensor for use with a reader is provided and can include an electrical component configured such that the coupling of a targeted substance to a surface of the electrical component changes an electrical characteristic of the electrical component. A protein immobilization structure can be disposed on the surface and can include an array of functionalized structures for interacting with a substance in a sample of a bodily fluid. Each functionalized structure can include a protein capable of binding to a targeted chemical substance or substance in the sample whereby an electrical reading can be obtained by a reader to determine the concentration level of the targeted substance in the sample.

7 Claims, 5 Drawing Sheets

Related U.S. Application Data

(60) Provisional application No. 61/907,363, filed on Nov. 21, 2013.

(51) Int. Cl.
*G01N 33/487* (2006.01)
*G01N 33/53* (2006.01)

(56) References Cited

U.S. PATENT DOCUMENTS

| | | | |
|---|---|---|---|
| 4,448,534 A | 5/1984 | Wertz et al. | |
| 4,735,906 A | 4/1988 | Bastiaans | |
| 4,767,719 A | 8/1988 | Finlan | |
| 4,789,804 A | 12/1988 | Karube et al. | |
| 4,822,566 A | 4/1989 | Newman | |
| 4,965,193 A | 10/1990 | Chen | |
| 4,977,247 A | 12/1990 | Fahnestock et al. | |
| 5,064,756 A | 11/1991 | Carr et al. | |
| 5,077,210 A | 12/1991 | Eigler et al. | |
| 5,111,221 A | 5/1992 | Fare et al. | |
| 5,182,005 A | 1/1993 | Schwiegk et al. | |
| 5,447,845 A | 9/1995 | Chu et al. | |
| 5,821,399 A | 10/1998 | Zelin | |
| 5,922,537 A | 7/1999 | Ewart et al. | |
| 6,280,586 B1 | 8/2001 | Wolf et al. | |
| 6,368,795 B1 | 4/2002 | Hefti | |
| 6,391,558 B1 | 5/2002 | Henkens et al. | |
| 6,548,263 B1 | 4/2003 | Kapur et al. | |
| 6,548,311 B1 | 4/2003 | Knoll | |
| 6,780,307 B2 | 8/2004 | Kidwell | |
| 8,508,100 B2 | 8/2013 | Lee et al. | |
| 8,728,844 B1 | 5/2014 | Liu et al. | |
| 9,377,456 B1 | 6/2016 | Herget et al. | |
| 9,702,847 B2 | 7/2017 | Herget et al. | |
| 9,766,201 B2 | 9/2017 | Herget et al. | |
| 9,944,969 B2 | 4/2018 | Knopfmacher et al. | |
| 9,963,733 B2 | 5/2018 | Knopfmacher et al. | |
| 2002/0127623 A1 | 9/2002 | Minshull et al. | |
| 2003/0073071 A1 | 4/2003 | Fritz et al. | |
| 2003/0109056 A1 | 6/2003 | Vossmeyer et al. | |
| 2003/0119208 A1 | 6/2003 | Yoon et al. | |
| 2006/0102935 A1 | 5/2006 | Yitzchaik et al. | |
| 2006/0197118 A1 | 9/2006 | Migliorato et al. | |
| 2006/0246426 A1 | 11/2006 | Woodbury et al. | |
| 2006/0286548 A1 | 12/2006 | Liposky | |
| 2007/0072187 A1 | 3/2007 | Blok et al. | |
| 2008/0012007 A1* | 1/2008 | Li | G01N 27/4145 257/40 |
| 2008/0199863 A1 | 8/2008 | Haake et al. | |
| 2009/0008247 A1 | 1/2009 | Chen et al. | |
| 2009/0020438 A1 | 1/2009 | Hodges | |
| 2009/0273354 A1 | 11/2009 | Dhirani et al. | |
| 2010/0025660 A1 | 2/2010 | Jain et al. | |
| 2010/0137143 A1 | 6/2010 | Rothberg et al. | |
| 2010/0194409 A1* | 8/2010 | Gao | C12Q 1/6825 324/693 |
| 2011/0068372 A1* | 3/2011 | Ren | G01N 27/414 257/194 |
| 2011/0306032 A1 | 12/2011 | Galiano et al. | |
| 2012/0032235 A1 | 2/2012 | Bikumandla | |
| 2012/0077692 A1 | 3/2012 | Hassibi et al. | |
| 2012/0088682 A1 | 4/2012 | Rothberg et al. | |
| 2012/0143027 A1 | 6/2012 | Phillips et al. | |
| 2012/0153262 A1 | 6/2012 | Paranjape et al. | |
| 2012/0153407 A1 | 6/2012 | Chang et al. | |
| 2012/0168306 A1 | 7/2012 | Hassibi et al. | |
| 2012/0208291 A1 | 8/2012 | Wayne et al. | |
| 2012/0256166 A1* | 10/2012 | Chen | H01L 21/02521 257/20 |
| 2012/0261274 A1 | 10/2012 | Rearick et al. | |
| 2012/0279859 A1 | 11/2012 | Rothberg et al. | |
| 2013/0089883 A1 | 4/2013 | Dallenne et al. | |
| 2013/0089932 A1* | 4/2013 | Wu | G01N 33/5438 436/501 |
| 2013/0096013 A1 | 4/2013 | Esfandyarpour et al. | |
| 2013/0105868 A1* | 5/2013 | Kalnitsky | G01N 27/414 257/288 |
| 2014/0057339 A1 | 2/2014 | Esfandyarpour et al. | |
| 2014/0134656 A1 | 5/2014 | Dortet et al. | |
| 2014/0191294 A1 | 7/2014 | Bikumandla et al. | |
| 2014/0231256 A1 | 8/2014 | Packingham et al. | |
| 2014/0349005 A1 | 11/2014 | Everett et al. | |
| 2015/0355129 A1 | 12/2015 | Knopfmacher | |
| 2016/0187332 A1 | 6/2016 | Herget et al. | |
| 2016/0187334 A1 | 6/2016 | Herget et al. | |
| 2016/0209356 A1 | 7/2016 | Herget et al. | |
| 2016/0266102 A1 | 9/2016 | Knopfmacher | |
| 2017/0058313 A1 | 3/2017 | Knopfmacher et al. | |
| 2017/0059508 A1 | 3/2017 | Knopfmacher et al. | |
| 2017/0212075 A1 | 7/2017 | Knopfmacher et al. | |
| 2017/0336348 A1 | 11/2017 | Herget et al. | |
| 2017/0342459 A1 | 11/2017 | Knopfmacher et al. | |

FOREIGN PATENT DOCUMENTS

| | | |
|---|---|---|
| WO | WO 2010/062001 | 6/2010 |
| WO | WO 2012/078340 | 6/2012 |
| WO | WO 2013/096404 | 6/2013 |
| WO | WO 2014/134431 | 9/2014 |
| WO | WO 2015/077632 | 5/2015 |
| WO | WO 2015/188002 | 12/2015 |
| WO | WO 2016/061453 | 4/2016 |
| WO | WO 2016/109569 | 7/2016 |
| WO | WO 2017/132095 | 8/2017 |
| WO | WO 2017/209839 | 12/2017 |
| WO | WO 2018/111234 | 6/2018 |

OTHER PUBLICATIONS

Dortet, Laurent et al., "Evaluation of the RAPIDECw CARBA NP, the Rapid CARB Screenw and the Carba NP test for biochemical detection of carbapenemase-producing Enterobacteriaceae", J Antimicrob Chemother, 70:3014-3022, 2015.

Dortet, Laurent et al., "Further Proofs of Concept for the Carba NP Test", Antimicrobial Agents and Chemotherapy, 58(2):1269, Feb. 2014.

Dortet, Laurent et al., "Rapid Identification of Carbapenemase Types in *Enterobacteriaceae* and *Pseudomonas* spp. by Using a Biochemical Test", Antimicrobial Agents and Chemotherapy, 56(12):6437-6440. Dec. 2012.

Kumar et al., "Sensitivity Enhancement Mechanisms in Textured Dielectric Based Electrolyte-Insulator-Semiconductor (EIS) Sensors," *ECS Journal of Solid State Science and Technology*, 4(3):N18-N23 (2015).

Nordmann, Patrice et al., "Strategies for identification of carbapenemase-producing Enterobacteriaceae". J Antimicrob Chemother, 68:487-489, 2013.

Poghossian et al., "Penicillin Detection by Means of Field-Effect Based Sensors: EnFET, Capacitive EIS Sensor or LAPS?", *Sensors and Actuators B*, 78:237 (2001).

Poirel, Laurent et al., "Rapidec Carba NP Test for Rapid Detection of Carbapenemase Producers". Journal of Clinical Microbiology, 53(9):3003-3008, Sep. 2015.

Schoning, Michael J., "'Playing Around' with Field-Effect Sensors on the Basis of EIS Structures, LAPS and ISFETs," *Sensors*, 5:126-138 (2005).

Dortet, Laurent et al., "Bloodstream Infections Caused by *Pseudomonas* spp.: How to Detect Carbapenemase Producers Directly from Blood Cultures", Journal of Clinical Microbiology, 52(4):1269-1273, Apr. 2014.

Estrela, Pedro et al., "Label-Free Sub-picomolar Protein Detection with Field-Effect Transistors," Analytical Chemistry, vol. 82, No. 9, May 1, 2010, 3531-3536.

Hammock, Mallory L et al., "Electronic readout ELISA with organic field-effect transistors as a prognostic test for preeclampsia," Advanced Materials, 26: 6138-6144. doi: 10.1002/adma.201401829.

(56) References Cited

OTHER PUBLICATIONS

Mathias, W. et al., "Selective Sodium Sensing with Gold-Coated Silicon Nanowire Field-Effect Transistors in a Differential Setup," ACS Nano 7, 5978-5983 (2013).
Salm, Eric et al., "Electrical Detection of Nucleic Acid Amplification Using an On-Chip Quasi-Reference Electrode and a PVC REFET," dx.doi.org/10.1021/ac500897t, *Anal. Chem.*, 2014, 86, 6968-6975.

* cited by examiner

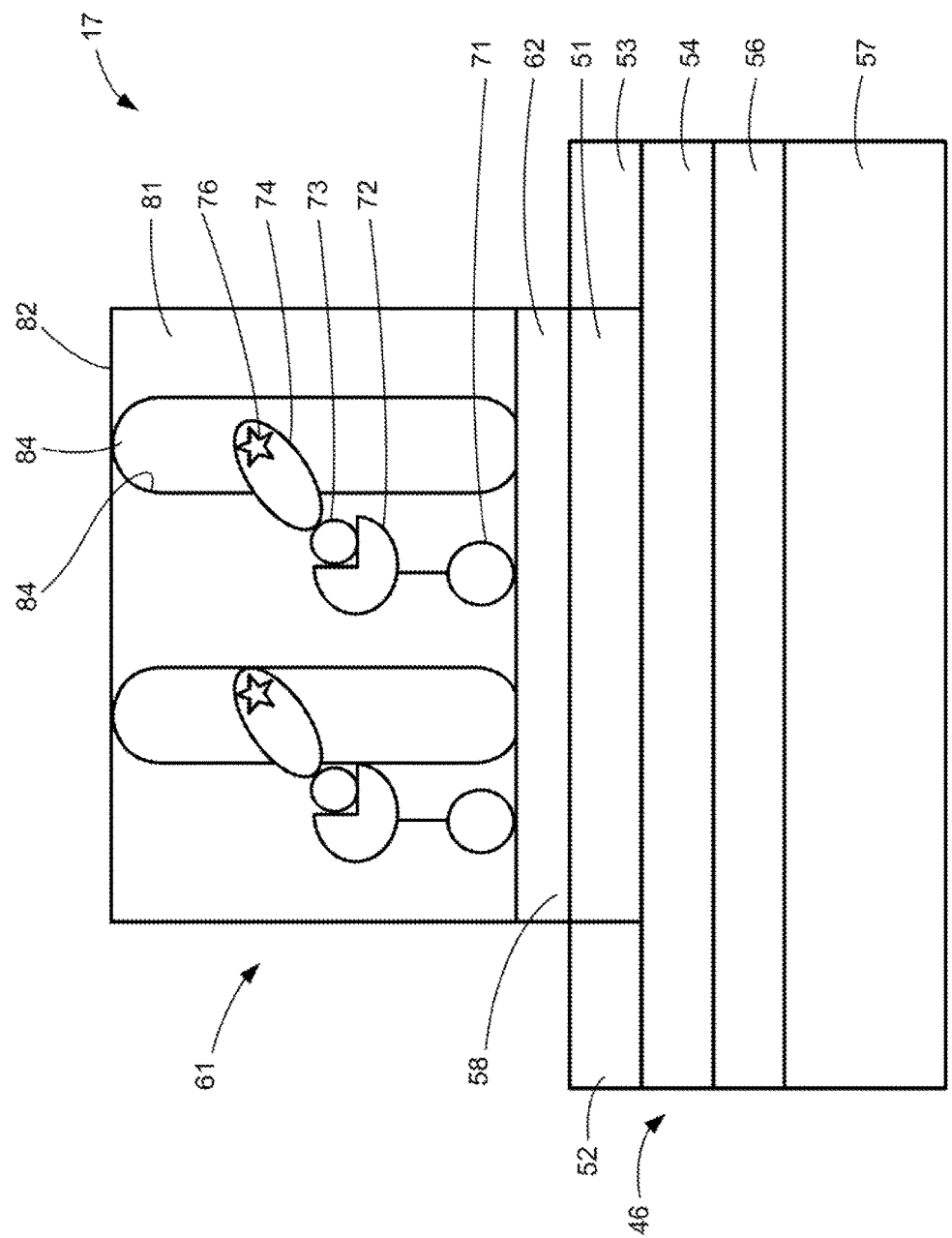

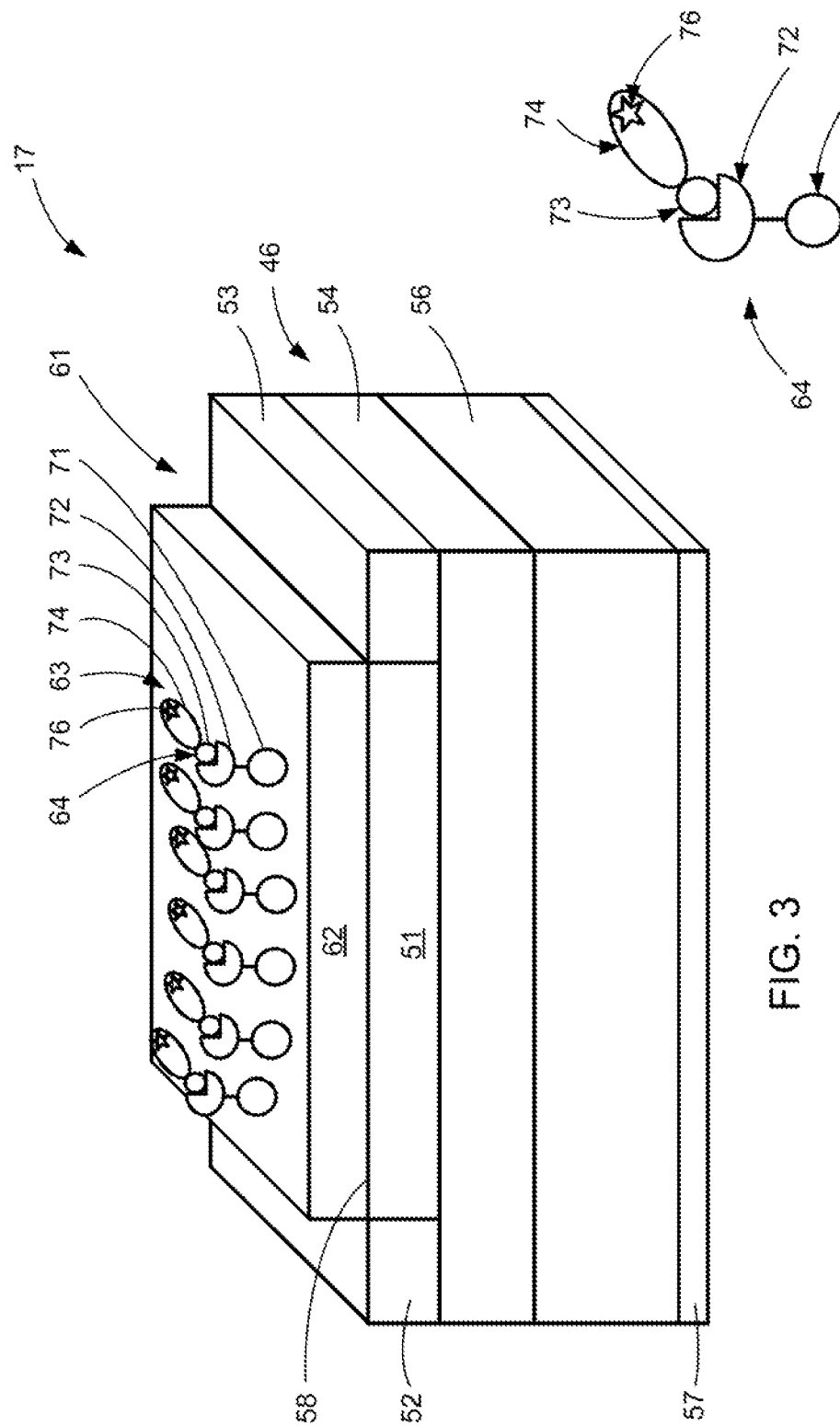

| Immobilization method | Surface for immobilization | Protein modification | Capturing mechanism |
|---|---|---|---|
| Physical adsorption | Polystyrene, Nitrocellulose, Glass coated with poly-Lys | Wild proteins | Physical adsorption |
| Immobilization using hydrogel | Glass plate | Wild proteins | Entrapment in gels |
| Hisx6-tag-mediated immobilization | Nickel-coated glass, Ni-NTA functionalized surface | Proteins fused with Hisx6 | Affinity between Hisx6 and Ni2+ |
| Immobilization using coiled coil interaction | OTS coated surface covalently bound with artificial polypeptide containing Leu zipper | Proteins fused with Leu zipper | Coiled coil association of a heterodimeric Leu zipper pair |
| Immobilization on Au surface | Au surface | Wild proteins containing Cys residues or recombinant ones with Cys introduced | Chemisorption of SH-groups on Au |
| Silane coupling method | Glass modified with bifunctional silane coupling reagents containing aldehyde | Wild proteins | Schiff's base linkage between aldehyde and amino groups |
| Transglutaminase mediated immobilization | Casein-grafted polyacrylic surface | Proteins fused with TGase specific peptide substrate | Acyl transfer reaction of Tgase |
| Streptavidin-mediated immobilization | Polystyrene or glass coated with streptavidin, or biotynylated BSA | Biotinylated protein | Affinity between streptavidin-biotin |
| FLAG-tag-mediated immobilization | Polystyrene coated with protein A and conjugated with anti-FLAG monoclonal antibody | Proteins fused with FLAG | Affinity between FLAG and anti-FLAG antibody |
| Glutathione / GST- mediated immobilization | Polystyrene coated with protein followed by covalently coupling with glutathione | Protein fused with GST | Affinity between glutathione and GST |
| Immobilization using PS-affinity peptide | Hydrophilic polystyrene | Protein fused with PS-affinity peptide | Affinity of the affinity peptide to PS surface |

FIG. 5

ELECTRICAL BIOSENSOR FOR DETECTING A SUBSTANCE IN A BODILY FLUID, AND METHOD AND SYSTEM FOR SAME

RELATED APPLICATIONS

This application is a continuation of International Application No. PCT/US20141066931 filed Nov. 21, 2014, which is a non-provisional application of Provisional Application No. 61/907,363 filed on Nov. 21, 2013, the entireties of which are incorporated by reference herein.

FIELD OF THE INVENTION

The present invention relates to electrical biosensors and more particularly, to electrical biosensors for detecting concentrations of a chemical substance present in a human.

BACKGROUND OF THE INVENTION

Current measurements of levels of substances in blood require blood tests in a clinical laboratory or a doctor's office. Such tests can be cumbersome, unpleasant and expensive, and cannot practically be accomplished on a daily basis.

Electrical biosensors have been provided. See, for example, U.S. Pat. No. 8,038,943 to Yoo et al., WO2012078340 to Bashir et al., and US20110201027 to Kim et al. Devices have also been provided for detecting the presence of drugs in a human. See, for example, US20050054942 to Melker et al. Devices have also been provided for detecting the presence of drugs in saliva. See, for example, EP1444508 to Kidwell.

There is a need for an improved device that allows noninvasive monitoring of various substances within a sample of bodily fluids using an electrical biosensor.

BRIEF DESCRIPTION OF THE DRAWINGS

The drawings described herein are for illustration purposes only and are not intended to limit the scope of the present disclosure in any way.

FIG. 2 is a side elevational view of the electrical biosensor of FIG. 1.

FIG. 3 is a perspective view of the electrical biosensor of FIG. 2, with the filter layer removed therefrom for simplicity.

FIG. 4 is an enlarged view of the protein immobilization structure of the electrical biosensor of FIG. 2.

FIG. 5 is a table listing various embodiments of the protein immobilization structure of the electrical biosensor of the present invention.

DETAILED DESCRIPTION OF THE INVENTION

The present invention can be utilized to detect the concentration of chemical and biological substances in a bodily fluid so as to determine the concentration of the chemical substance or biological substance in the patient The chemical substances can include or be therapeutic drugs. The biological substances can include biomarkers. The bodily fluid can include human saliva, urine, tears, nasal secretions, stools, male ejaculate or any combination of the foregoing. In one embodiment, the bodily fluid can include blood, serum, plasma or any combination oldie foregoing or any combination of the bodily fluids listed herein. In one embodiment, the bodily fluid can be any bodily fluid other than blood in which the targeted drug or other substance appears in a concentration that reliably represents the concentration that the targeted drug or other substance appears in the patient's blood. In one embodiment, the bodily fluid can be any bodily fluid other than blood in which the targeted drug or other substance appears in a concentration that directly or inversely correlates to the concentration that the targeted drug or other substance appears in the patient's blood. The invention is well suited for use in home care and for example can be used by a patient at home or otherwise away from a clinical setting to detect the concentration of a therapeutic drug or other targeted substance in a sample of saliva taken from the patient.

Figure 1:
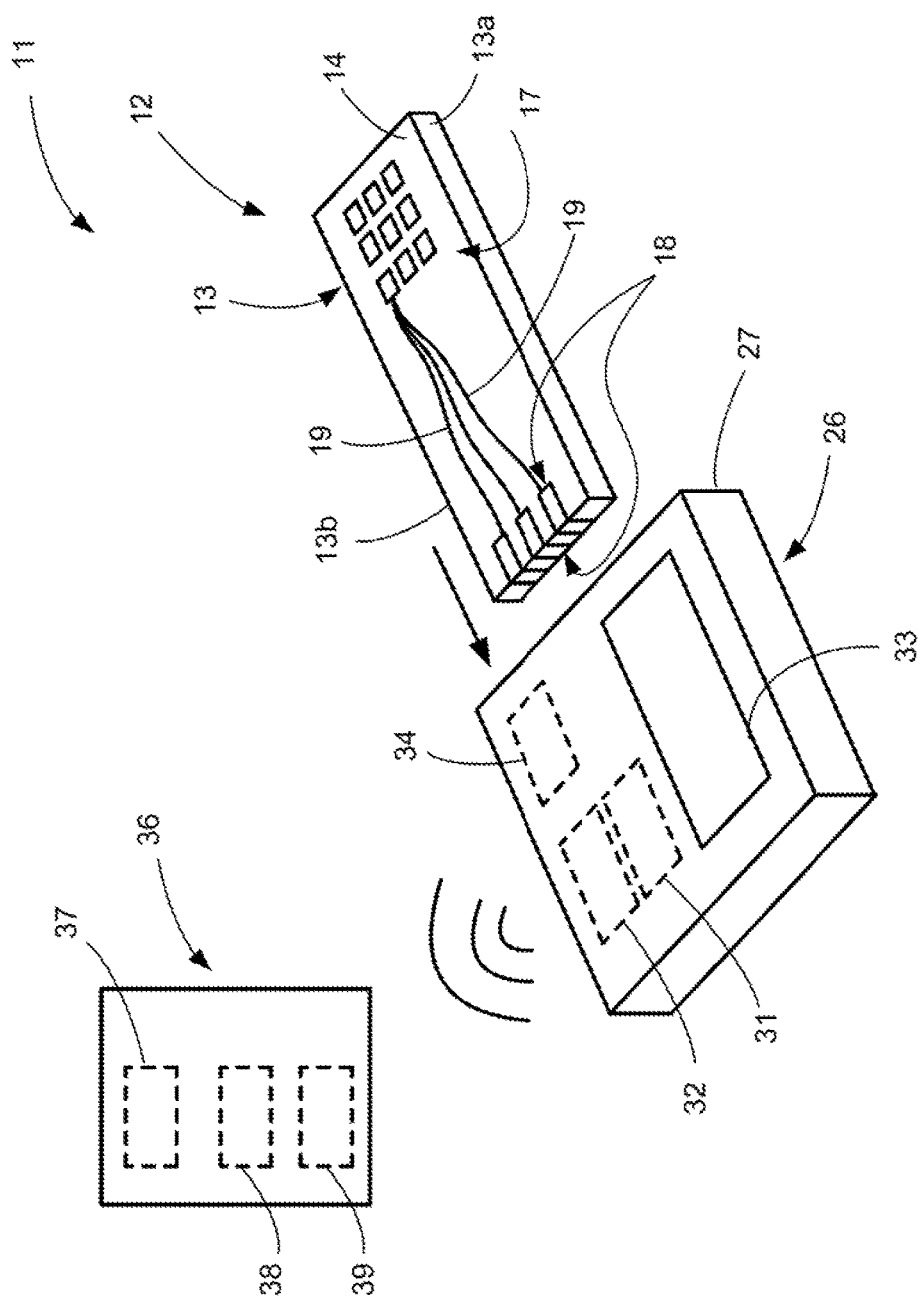
FIG. 1 is a perspective view of a system utilizing the reader and strip with electrical biosensor of the present invention.

One embodiment of system 11 of the present invention is illustrated in FIG. 1. System 11 therein includes a disposable strip 12 formed from a body 13 made from any suitable material such as plastic. In one embodiment, the body 13 is rectangular in shape when viewed in plan has opposite first and second end portions 13a and 13b and a surface 14 extending between the end portions 13a, 13b. At least one and as shown a plurality of electrical biosensors 17 of the invention are mounted in any suitable way such as an adhesive on surface 14 at the first end portion 13a, and the end portion 13a is sized and dimensioned so as to fit within a human mouth so as to collect a sample of saliva on the biosensors 17. The invention further allows testing of saliva that has been expectorated into a container, thereby avoiding the need to put the device in the mouth. Any suitable number of electrical biosensors 17 can be carried by or mounted on the body of the device 13, and in the illustrated embodiment a plurality of nine electrical biosensors arranged in a 3×3 array are mounted on the first end portion 13a of the body.

A plurality of contact elements or electrodes 18 are provided on the second end portion 13b of the strip 12 for each electrical biosensor 17 disposed on the first end portion 13a of the strip 12. The second end portion 13b of the strip can be of any suitable size and dimension and in one embodiment is sized and dimensioned similar to the first end portion 13a of the strip. Each electrode 18 is made from any suitable conductive material such as copper, is electrically isolated from the remaining electrodes on the body 13 and is electrically connected to the respective biosensor by a suitable electrical lead such as a conductive trace or wire 19. In the illustrated embodiment, three electrodes 18 are electrically coupled to each electrical biosensor 17, and for simplicity only the three electrodes 18 relating to one of the biosensors 17 are shown in FIG. 1.

System 11 further includes a suitable read-out device or reader 26 for detecting and analyzing the analog electrical signals provided by each of the electrical biosensors 17 on strip 12 and transmitted to electrodes 18 by means of the conductive leads or traces 19. Reader 26 can be of any suitable size and shape and in one embodiment is handheld in size so as to have a size and shape suitable for being held in a mature human hand. In one embodiment, the reader has a size and shape in plan that approximates or is less than the palm of a human hand, for example the palm of a full-sized human adult. In one embodiment, the reader has a size and shape approximating the size and shape of a smart phone or other handheld communication device.

In one embodiment, the reader 26 includes a housing 27 made from any suitable material such as metal or plastic having an opening or port not shown) for accessing a socket or recess (not shown). Such opening and socket are sized and shaped to receive second end portion 13b of the strip body 13, and at least a portion of each of the plurality of electrodes IS provided on the second end portion 13b of the strip 12. The reader further includes electrical components for receiving, digitizing and analyzing the analog electrical signals received from the plurality of electrodes 18, and thus the electrical biosensors 17. Such electrical components can include a suitable computer processor or central processing unit 31 electrically coupled to the electrical pickups of the reader 26 (not shown) that electrically engages the strip electrodes 18. Reader 26 can further include suitable storage or memory 32, electrically coupled to the processor 31, for storing computer data. A suitable display 33 can be included in the reader for displaying desired information. The display 33 can be a touch screen, for additionally serving as an input device or terminal. A transmitter or transceiver 34 can be included in the housing 27, and electrically coupled therein with processor 31, for wirelessly transmitting or receiving information between the reader 26 and a suitable remote device.

The system 11 of the invention can include a suitable remote device for wirelessly communicating, with reader 26. Such remote device 36 can include a remote server, a remote mobile device, a remote computer or any combination of the foregoing. Such remote device 36 can include, as illustrated in FIG. 1, electrical components for receiving and analyzing the electrical signals received from reader 26, which can include a suitable computer processor or central processing unit 37, The remote device 36 can further include suitable storage or memory 38, that is electrically coupled to the processor 37, for storing computer data, and a transmitter or transceiver 38, that is electrically coupled therein with processor 37, for wirelessly transmitting or receiving information between the remote device 36 and reader 26, it is appreciated that the receiver 26 can be wired directly or wirelessly connected to any suitable local computing device, such as a mobile device or a computer, which in turn can wirelessly communicate with a suitable remote device 36.

Electrical biosensor 17, which can also be an electrical device or sensor, can be of any suitable type. In one embodiment, the biosensor 17 includes any suitable electrical component 46 having an electrical characteristic and being configured such that the coupling of the chemical substance being measured, for example a therapeutic drug, to the electrical component changes the electrical characteristic of the electrical component. In one embodiment, the electrical component has a surface, and the coupling of the chemical substance being measured to the surface of the electrical component changes the electrical characteristic, of the electrical component. The electrical component can include, without limitation, a transistor, a capacitor, a resistor and an inverter.

In one embodiment, the electrical component 46 is any suitable transistor, and in one embodiment the electrical component 46 is a field effect transistor or FET (see FIGS. 2-3). The FET can be of any suitable type, and in one embodiment includes a semiconducting layer 51 doped with a n-type or p-type material. A source or source electrode 52 and a drain or drain electrode 53 are formed in spaced-apart positions on two sides of the semiconducting layer 51. First electrode or source 52 and second electrode or drain 53 are each doped having an opposite polarity to the semiconducting layer 51. A suitable dielectric layer 54, such as an oxide layer, underlies the semiconducting layer 51 and the source 52 and drain 53. A gate electrode 56 underlies the dielectric layer 54. In one embodiment, each of source 52, drain 53 and gate electrode 56 is electrically coupled, for example by means of a conductive lead 19, to one of the contact electrodes 18 provided on strip 12. A substrate layer 57 made from any suitable material such as plastic or glass serves as a support layer to biosensor 17, and as a support to the foregoing structure, and in one embodiment underlies gate electrode 56. In one embodiment, the semiconducting layer 51 has a surface 58 that is opposite to the surface to which dielectric layer 54 is adhered.

A suitable protein immobilization structure is coupled to the electrical component 46 and in one embodiment is disposed on surface 58 of the electrical component 46 for tethering the plurality of desired proteins to surface 58 or otherwise to the electrical component 46. A variety of structures or means can be utilized to functionalize a binding protein to the electrical component 46, such as to surface 58 of the electrical component. Three suitable categories of protein immobilization structures include physical immobilization, which can include hydrogen bonding, ionic bonding, Van der Waals forces and hydrophobic interactions; covalent immobilization, which can include amine, thiol, carboxyl and epoxy chemistry, photoactive chemistry, Diels-alder cycloaddition, "click" chemistry and peptide, standinger or R-Oxo semicarbazone litigation; and bio-affinity immobilization, which can include an avidin-biotin system, his-tag system, DNA directed and an affinity capture ligand system.

In one embodiment of a bio-affinity immobilization system, the protein immobilization structure 61 includes a passivation or functionalization layer 62 of any suitable type overlying the electrical component or transistor 46. In one embodiment, the passivation layer is a high-κ dielectric atomic layer deposition (ALD) layer, which can be made from aluminum oxide, titanium oxide, zirconium oxide, yttrium oxide, silicon oxide, tantalum oxide, hafnium oxide, silicon nitride, any combination of the foregoing or any other suitable material.

The protein immobilization structure 61 includes an array 63 of functionalized structures 64 for interacting with the fluid sample being tested. Although the functionalized structures can be of any suitable type, in one embodiment each functionalized structure includes a protein capable of binding or bonding to the targeted chemical or biological substance. The targeted chemical substance can be any drug, a therapeutic drug, any substance found in saliva or any substance found in a bodily fluid. In one embodiment, the targeted chemical substance can be any suitable drug, now known or to be developed in the future. Other suitable targeted substances are included in the scope of the invention, as well as corresponding binding proteins for such other targeted substances. In one embodiment, each functionalized structure includes biotin, for bonding to the binding protein.

One embodiment of a functionalized structure 64 suitable for bonding to passivation layer 62 of electrical biosensor, as illustrated in FIGS. 2-4, includes a suitable functionalization entity such as a nano-particle 71 for adhering to the passivation or functionalization layer 62. Protein immobilization structure 61 includes a portion for adhering to passivation layer 62 that includes nano-particles 71. Suitable nano-particles 71 can be made from any suitable material such as metal. Metal nano-spheres, nano-rods and other similar nano-structures can be utilized in the functionalized structure 64 for adhering to passivation layer 62. Streptavidin/DNA 72 is bonded to the nano-particle 71, and biotin 73 is bonded to the streptavidin/DNA for receiving the suitable binding protein or molecule 74, having a binding site 76, for bonding to the targeted chemical substance.

Each electrical biosensor 17 can additionally include a layer or filter 81 disposed over the array 63 of functionalized structures 64 for limiting by size particulates in the test sample, for example human saliva, capable of engaging the binding protein 74 (see FIG. 2). Layer 81 can be of any suitable type and in one embodiment is a porous transport layer made from any suitable material such as a polymer, and can be of any suitable thickness for example 0.1 millimeters. The transport membrane or layer 81 can overlie the array 63 of functionalized structures 64, and include a top surface 82. The layer 81 can be micro-porous and provided with a plurality of openings 83 in surface 82 that each communicate with a respective channel or pore 84 in the layer that extends from the top surface to a respective binding site 76 in the array 63. The openings 83 and micro-pores 84 are sized to permit passage there through of the targeted drug or other chemical substance, and restrict entry into the openings and bores of larger sized molecular structures and particulates present in the bodily fluid. Each of the openings 83 and micro-pores 84 can be of any suitable size. In one embodiment, each of the micro-pores has a transverse dimension, width or diameter ranging from 0.5 to 5.0 micrometers, and in one embodiment less than one micrometer. Some or all of the openings 83 and micro-pores 84 can have the same or equal transverse dimension, width or diameter. In one embodiment, the transverse dimension, width or diameter of one or more of the micro-pores 84 reduces as it extends from the opening 83 towards the binding protein 74, and as such the micro-pore is bigger or wider at the opening 83 than narrows or tapers inwardly as it approaches binding protein 74 and binding site 76. In one embodiment, the openings 83 and corresponding micro-pores 84 are disposed in an array that is substantially similar to array 63, and as such an opening 83 and micro-pore 84 are provided for each binding site 76 of each functionalized structure 64. The filter or layer 81 can thus serve as a transport layer for the targeted substance to the binding protein 74.

In one method of operation and use, a patient or user is provided with one or more strips 12 for periodically monitoring concentrations of a targeted chemical substance, such as a therapeutic drug, in the user's body. The one or more strips 12 are configured, either at the time of manufacture or at some other time prior to use, to provide a binding protein 74 on the free end of each functionalized structure 64 that binds to the targeted therapeutic drug. The monitoring can be done daily or at some other frequency suggested or prescribed by a doctor or other medical personnel. The user can additionally be provided with a reader 26. In one embodiment, the user dips the first end portion 13a of a strip 13 into a sample of saliva or other bodily fluid, for example saliva removed from the user's mouth. The user can also introduce the first end portion 13a of the strip into the user's mouth and cause the plurality of sensors 17 provided on the first end portion 13a of the strip of engage saliva present in the mouth.

The porous membrane or filter 81, for example provided on the top of each sensor 17 and overlying the may 63 of functionalized structures 64, is provided with openings 83 and micro-pores 84 therein that are sized to permit passage of the targeted drug or other chemical substance, and preclude the passage through openings 83 and micro-pores 84 of larger sized structures or particulates present in the saliva. Exemplary sizes for openings 83 and micro-pores 84 are set forth above. In this manner, the number of analytes and structures in the saliva that can access the binding site 76 is desirably limited so as to facilitate access of the targeted substance to the binding site and thus increase the accuracy of the concentrations measurements taken by the electrical sensors 17.

The engagement to or binding of the targeted drug or other substance to the binding site 76 causes the targeted substance to interact with the electrical component 46 so as to change the electrical characteristic of the electrical component The changeable electrical characteristic can include, for example, the voltage, current, resistance or capacitance of the electrical component 46. In one embodiment, the electrical characteristic of component 46 changes as a function of the concentration of the targeted substance in contact with the component 46. In one embodiment of transistor or FET 46, the binding of the targeted drug to the binding protein 74 provided on the free end of each functionalized structure 64 can change the source-drain current, that is the current flow between the source electrode 52 and drain electrode 53, or shift the threshold "turn-on" voltage, that is the gate voltage at which current begins to flow between the source electrode and the drain electrode, of the FET 46. In one embodiment, the change in the voltage between the source and drain electrodes can be monitored. The current or voltage change in the FET 46 can be detected by comparing the current-voltage characteristics of the FET 46 during operation to the current-voltage characteristics known before the binding event or by comparing the current-voltage characteristics of the FET 46 during operation to a similar FET which does not bind the target drug or other substance. The change occurs during the binding event because the drug or other substance alters the electric field within the FET 46, thereby changing the current-voltage characteristics of the electrical device 46. The greater the number of proteins 74 that bind to the targeted substance in the bodily fluid, the greater the change in the electrical characteristic of the FET 46. Since the source 52, drain 53 and gate electrode 56 of each electrical biosensor 17 is electrically coupled to an contact electrode 18 provided on the second end portion 13b of the strip 12, the change in the electrical characteristic of each electrical component 76 can be measured at such contact electrodes 18. The greater the number of sensors 17 provided on a strip 12, the greater the number of independent measurements are taken by the strip and thus, for example by averaging the independent measures, the greater the accuracy of the aggregate or overall measurement provided by the strip 12.

The user can insert the second end portion 13b of the strip 12 into reader 26 to permit a real time determination of the concentration of the targeted substance in the bodily fluid of the patient. The reader 26, alone or in conjunction with another suitable computing device, can be calibrated to convert the change in electrical response of the electrical component 46 into a concentration level of the targeted drug or other substance. In one embodiment, a suitable algorithm can be provided in software and stored on memory 32 of the reader 26 or programmed onto a chip provided on the reader 26 so as to permit processor 31 of the reader to manipulate or process the plurality of measurements provided by the respective plurality of sensors 17 on the strip 12 and arrive at an immediate numerical concentration of the targeted substance in the saliva. The concentration level of the targeted drug or other substance can be provided on reader display 33, or otherwise indicated on the reader 26, so as to provide the user with a real time concentration reading of the targeted substance, it is appreciated that some or all of such algorithm, or similar calculations, can be performed on remote device 36 or elsewhere remotely and the resulting concentration reading made available to the user, medical personnel, others or any combination of the foregoing. For example, some or all of such algorithm can be provided in software and stored on memory 33 of remote device 36 so as to permit processor 37 of the remote device to unilaterally or in conjunction with reader 26 or other computing devices to manipulate or process the plurality of measurements provided by the respective plurality of sensors 17 on the strip 12 and arrive at a numerical concentration of the targeted substance in the saliva. The resulting concentration reading, and other related information provided by the user's medical personnel, can be provided to user through reader 26 or any other computing or other device.

In one embodiment, the user can upload the measurements from strip 12 or concentration levels calculated by reader 26, for example through the cloud, to medical personnel for evaluation. The uploading can be performed by reader 26 or any other suitable wireless or other computing device. For example, the drug concentration levels or data obtained by reader 26 can be provided to a personalized weblog, along with in some embodiments personalized information provided by the user, stored or provided on a remote computing device 36 such as a remote server of the type disclosed above. Such uploading or other communication with remote personnel or devices can occur instantaneously upon the completion the computations performed by the reader 26 following the insertion of the strip 12 into reader 26, or on some other occurrence initiated by the user. Suitable data analytics can be performed at the remote device 36 or other suitable remote computing device and visualized for medical personnel, the patient or both.

In the embodiment where the targeted substance is a drug, such periodic home monitoring and feedback of drug concentration levels may facilitate the maintenance of desirable therapeutic and non-toxic drug levels so as to hinder undesirable side effects. in this regard, for example, upon reviewing the concentration levels provided by strips 12 and reader 26, medical personnel may adjust the dose of the measured drug or other substance or provide other specific feedback to the user. Alternatively, or in addition, the user or caretakers of the user may adjust drug dosages based upon pre-specified guidelines or feedback from software parameters previously established by the medical personnel. The invention desirably permits the concentration levels of such drugs to be easily monitored at a desired frequency. The adjustment in drug concentration levels can additionally serve to minimize the occurrence of toxicity or other side effects in the user or patient.

The testing system of the present invention permits non-invasive measurement and tracking of levels of therapeutic drugs or other chemical substances in saliva or other bodily fluids. The system does not require pricking of a finger to obtain a fluid sample for testing, and facilitates the daily or other periodic monitoring of drug or other substance levels. The system allows the quantifying of drug levels in saliva or other bodily fluids and minimizes if not avoids the need for repeated invasive sampling of blood.

Other embodiments of the protein immobilization structure for use with the electrical biosensor and strip of the present invention can be provided. Suitable protein immobilization structures for use with the invention are set forth in FIG. 5, and other suitable immobilization structures can be provided. In FIG. 5, the column entitled "Surface for immobilization" refers to a surface of a layer of material that overlies electrical component 46, for example a layer of material overlying passivation layer 62 of electrical biosensor 17. Such immobilization surface can include a metallic layer, an organic layer, a self-assembled monolayer, a polymer layer, an atomic layer deposition layer and a chemical vapor deposition layer. The column entitled "Protein modification" in FIG. 5 refers to the types of proteins that can be immobilized using a given immobilization method, and the column entitled "Capturing mechanism" in FIG. 5 refers to the mechanism by which an analyte binds to an immobilized protein.

Figure 6:
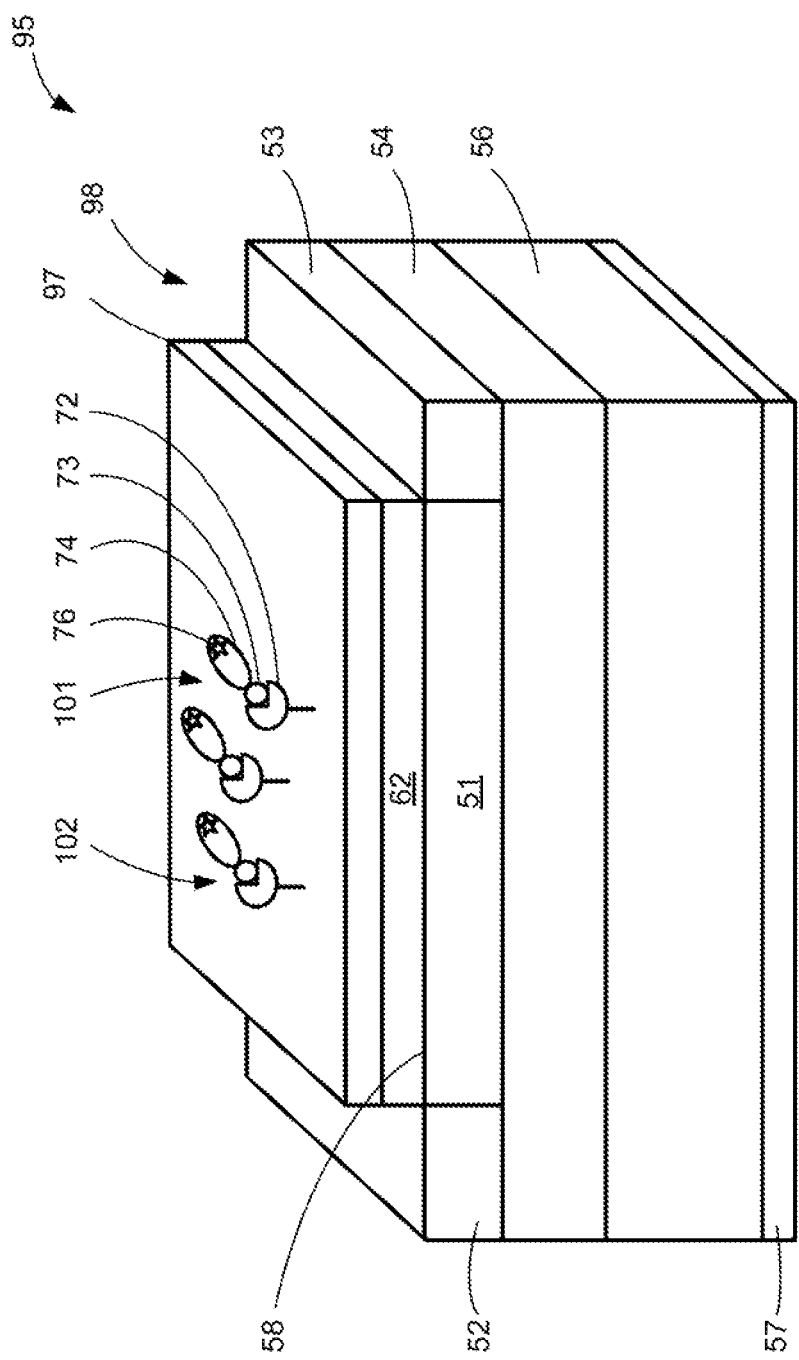
FIG. 6 is a perspective view, similar to FIG. 3, of another embodiment of an electrical biosensor of the present invention.

In one embodiment of the invention of a bio-affinity immobilization, a protein immobilization structure can be provided that utilizes a metal layer for adhering to the passivation layer of the electrical biosensor. Electrical biosensor 96, illustrated in FIG. 6, is substantially similar to biosensor 17 and like reference numerals have been used to describe like components of biosensors 17 and 96. Instead of the functionalization entity elements or non-particles 71 of biosensor 17, the electrical biosensor 96 includes a functionalized metal thin film 97 overlying passivation or ALD layer 62. The layer or film 97 can be made from any suitable metal such as gold. En this regard, protein immobilization structure 98 of biosensor 96 includes a portion comprised of a suitable metal layer for adhering to ALD or passivation layer 62.

Protein immobilization structure 98 includes an array 101, which can be substantially similar to array 63, of functionalized structures 102 for interacting with the fluid sample being tested. The functionalized structures 102 can be of any suitable type, including any of the functionalized structures disclosed above or herein. One embodiment of a functionalized structure 102 suitable for bonding to passivation layer 62, by means of film or layer 97, includes streptavidin/DNA 72 bonded to the metal or other layer 97 and biotin 73 bonded to the streptavidin/DNA. The biotin 73 receives a suitable binding protein or molecule 74, for example any of the proteins or molecules discussed above or herein. The binding, protein has a binding site 76, for bonding to the targeted chemical substance.

Electrical biosensor 96 can additionally include a layer or filter 81 disposed over the array 101 of functionalized structures 102. Filter 81 can be of any suitable type, including as discussed above, and can serve any of the purposes discussed above with respect to filter 81. For simplicity, filter 81 is not included in FIG. 6. One or a plurality of electrical biosensors 96 can be provided on a strip, for example as disclosed above with respect to electrical biosensor 17 and strip 12.

In one method of operation and use, a strip 12 having a plurality of electrical biosensor 96 disposed thereon can operate in the same manner as discussed above with respect to electrical biosensor 17 and strip 12 for determining the concentration of targeted drugs or other chemical substances in a sample of saliva or other fluid. Such operation can include a suitable reader, such as reader 26, and can include other suitable computing devices as discussed above.

In one embodiment, an electrical biosensor for use with a reader to detect a concentration level of a therapeutic drug in a sample of a bodily fluid is provided, and can include an electrical component having an electrical characteristic and a surface, the electrical component being configured such that the coupling of the drug to the surface changes the electrical characteristic of the electrical component, the electrical component having first and second electrodes adapted to electrically couple to the reader for obtaining an electrical reading from the electrical component that is a function of the electrical characteristic, a protein immobilization structure disposed on the surface of the electrical component and including an array of functionalized structures for interacting with the sample, each functionalized structure including a protein capable of binding to the therapeutic drug in the sample whereby an electrical reading can be obtained by the reader to determine the concentration level of the therapeutic drug in the sample of the bodily fluid.

The electrical component can be selected from the group consisting of a transistor, a capacitor, a resistor and an inverter. The protein immobilization structure can include a high-κ dielectric ALD layer. The high -κ dielectric ALD layer can be selected from the group consisting of aluminum oxide, titanium oxide, zirconium oxide, yttrium oxide, silicon oxide, tantalum oxide, hafinum oxide and silicon nitride. The protein immobilization structure can include a portion selected from the group consisting of nanoparticles and a metal layer for adhering to the ALD layer. Each functionalized structure can include biotin far bonding to the protein. The electrical biosensor can further include a layer disposed over the array of functionalized structures for limiting by size particulates in the bodily fluid capable of engaging the protein. A plurality of the electrical biosensors can be carried b a disposable strip.

In one embodiment, a method for detecting a concentration level of a therapeutic drug in a sample of a bodily fluid can be provided, and can include providing an electrical component having an electrical characteristic, interacting the sample with the electrical component so as to couple the drug to the electrical component and change the electrical characteristic of the electrical component and measuring the electric characteristic so as to determine the concentration of the drug in the sample.

The electrical component can be selected from the group consisting of a transistor, a capacitor, a resistor and an inverter. The method can further include a protein immobilization structure disposed on a surface of the electrical component and including an array of functionalized structures for interacting with the sample, each functionalized structure including a protein capable of binding to the therapeutic drug in the sample.

The invention claimed is:

1. An electrical biosensor for use with a reader to detet a concentration level of a substance in a sample of a bodily fluid, the electrical biosensor comprising:
    an electrical component having an electrical characteristic and a surface, the electrical component being configured such that the coupling of the substance to the surface changes the electrical characteristic of the electrical component, the electrical component having first and second electrodes adapted to electrically couple to the reader for obtaining an electrical reading from the electrical component that is a function of the electrical characteristic; and
    a protein immobilization structure disposed on the surface of the electrical component and including a high-κ dielectric ALD layer, nanoparticles that adhere to the high-κ dielectric ALD layer, and an array of functionalized structures for interacting with the substance, wherein each functionalized structure includes a protein capable of binding to the substance and is bonded to one of the nanoparticles that is adhered to the high-κdielectric ALD layer, whereby an electrical reading can be obtained by the reader to determine the concentration level of the substance in the sample of the bodily fluid.

2. The electrical biosensor of claim 1, wherein the electrical component is selected from the group consisting of a transistor, a capacitor, a resistor and an inverter.

3. The electrical biosensor of claim 1, wherein the nanoparticles are selected from the group consisting of metal nano-spheres and nano-rods.

4. The electrical biosensor of claim 3, wherein the high-κ dielectric ALD layer is selected from the group consisting of aluminum oxide, titanium oxide, zirconium oxide, yttrium oxide, silicon oxide, tantalum oxide, hafnium oxide and silicon nitride.

5. The electrical biosensor of claim 1, wherein each functionalized structure comprises a DNA-streptavidin structure that is bonded to each nanoparticle that is adhered to the high-κ dielectric ALD layer.

6. The electrical biosensor of claim 5, wherein each DNA-streptavidin structure is bonded to biotin that receives the protein capable of binding to the substance.

7. A plurality of the electrical biosensors of claim 1 carried by a disposable strip.

* * * * *